(12) United States Patent
Kostka

(10) Patent No.: US 9,480,254 B2
(45) Date of Patent: *Nov. 1, 2016

(54) SYSTEMIC MITIGATION OF ENVIRONMENTAL STRESS ON PLANTS AND THE FRUIT THEREOF

(75) Inventor: Stanley J. Kostka, Cherry Hill, NJ (US)

(73) Assignee: Aquatrols Corporation of America, Paulsboro, NJ (US)

(*) Notice: Subject to any disclaimer, the term of this patent is extended or adjusted under 35 U.S.C. 154(b) by 851 days.

This patent is subject to a terminal disclaimer.

(21) Appl. No.: 12/386,395

(22) Filed: Apr. 17, 2009

(65) Prior Publication Data

US 2009/0280985 A1  Nov. 12, 2009

Related U.S. Application Data

(60) Provisional application No. 61/126,973, filed on May 8, 2008.

(51) Int. Cl.
*A01N 43/02* (2006.01)
*A01P 21/00* (2006.01)
*A01N 43/16* (2006.01)
*A01N 31/02* (2006.01)

(52) U.S. Cl.
CPC .............. *A01N 43/16* (2013.01); *A01N 31/02* (2013.01)

(58) Field of Classification Search
CPC ... A01N 31/02; A01N 43/16; A01N 2300/00
USPC ........................................................ 504/140
See application file for complete search history.

(56) References Cited

U.S. PATENT DOCUMENTS

| | | | |
|---|---|---|---|
| 5,958,104 A * | 9/1999 | Nonomura et al. | 71/11 |
| 6,350,788 B1 * | 2/2002 | Herold et al. | 516/204 |
| 6,460,290 B1 * | 10/2002 | Moore et al. | 47/48.5 |
| 6,479,437 B1 | 11/2002 | Bratz et al. | |
| 6,851,219 B2 | 2/2005 | Kostka et al. | |
| 7,399,730 B2 * | 7/2008 | Kostka et al. | 504/362 |
| 7,541,386 B2 | 6/2009 | Kostka et al. | |
| 2003/0073583 A1 * | 4/2003 | Kostka et al. | 504/362 |
| 2003/0167683 A1 * | 9/2003 | Moore | C05G 3/06 47/48.5 |
| 2004/0146617 A1 * | 7/2004 | Schrader | 426/335 |

* cited by examiner

*Primary Examiner* — Johann R Richter
*Assistant Examiner* — Courtney Brown
(74) *Attorney, Agent, or Firm* — Ohlandt, Greeley, Ruggiero & Perle, L.L.P.

(57) ABSTRACT

Systemic mitigation of the heat stress damage to plants and pre-harvest fruit caused by environmental stress on the plant and fruit is realized by applying to the root zone of the plant a bioefficaciously effective amount of a composition selected from the group consisting of ethylene oxide-propylene oxide block copolymer, alkyl ethers of ethylene oxide-propylene oxide block copolymer, alkyl polyglycoside, and combinations thereof.

20 Claims, No Drawings

SYSTEMIC MITIGATION OF ENVIRONMENTAL STRESS ON PLANTS AND THE FRUIT THEREOF

The present application claims the benefits accorded under 35 U. S. C. 119(e) of prior provisional application No. 61/126,973 filed May 8, 2008.

FIELD OF THE INVENTION

The present invention generally relates to a method for systemically mitigating environmental stresses on fruit and certain vegetable crops; especially a systemic method for reducing the negative effects of environmental stresses such as heat stress, radiation, and/or drought. This is accomplished by the application to the plant root zone environment of ethylene oxide-propylene oxide block copolymer, alkyl ethers thereof, alkyl glycosides, and/or combinations thereof as set forth herein. This process is especially efficacious in significantly reducing the damage to fruit caused by sunburn, heat stress, and other environmental stresses such as a deficiency of water.

BACKGROUND OF THE INVENTION

The sun's light and heat can cause considerable damage to fruit and vegetable crops. One type of damage is sunburn, the visible damage that begins on the fruit surface. A different type of damage, heat stress, can also cause significant loss. Heat stress is often less noticeable than sunburn, but plants undergoing heat stress respond by shutting down the photosynthetic process. When this occurs in late spring, plants can drop some of their fruit load. Heat stress also manifests itself as reduced foliar flushes, especially in young trees. While sunburn and heat stress are different, they both usually result from excessive exposure to infrared light from the sun and can be equally devastating in reducing crop quality and yield.

Sunburn has been identified to cause multi-million dollar crop losses. Apple producers have reported that sunburned damaged fruit is normally the major source of cullage and sunburn has damaged up to 50% of a harvested crop; an extremely important problem for the industry. In orchards for example, the shift to high-density plantings on size-controlling (dwarfing) rootstocks has resulted in smaller trees with less foliage to protect the fruit from solar radiation. Also, many new cultivars, e.g., "Fuji", "Granny Smith", "Jonagold", "Gala", and "Braeburn" are susceptible to sunburn. Consequently, the incidence of sunburn crop losses have increased as the shift to these new cultivars has occurred. It is being predicted that sunburn damage will continue to increase in the coming years as a result of the depletion of the stratospheric ozone layer leading to an increase in the ultraviolet-B radiation reaching the earth's surface and global warming.

Many variables play a role in the amount of sunburn damage that occurs in fruit crop such as meteorological elements, e.g., air temperature, relative humidity, the wind speed, direction and turbulence; the variety and physiological condition of the plants which influence the tree vigor, fruit size, transpiration efficiency, solar absorption, interception of solar energy, temperature tolerance, heat conductivity of the fruit, fruit coefficient of convective heat exchange, photo-stability, tolerance to ultraviolet radiation, degree of adaptation, and sensitization to the environment; the soil environmental condition, e.g., nutrient and water availability; air circulation; tree management, e.g., pruning practices; and so on. Thus, the amount of sunburn damage that a crop experiences is subject to a large range of complex, interacting factors.

Apple studies have distinguished three types of sunburn on fruit. One type is often noticed as a necrotic spot on the sun-exposed side of the fruit, and results from the thermal death of cells in the peel when the surface temperatures of the fruit reach about 126° F. Necrosis can begin in only 10 minutes at or above this temperature. Sunlight is not necessary for this condition to occur for it can result from high thermal exposure alone. Because of cell membrane damage, electrolyte leakage increases significantly in the skin or peel from fruit with necrosis.

The second type is called "sunburn browning"; a sub-lethal event that results in a yellow, bronze, or brown spot on the sun-exposed side of the fruit. Sunburn browning in apples occurs when the fruit surface temperatures reach from about 115° F. to 120° F. in the presence of sunlight. This threshold temperature required for sunburn browning is cultivar dependent. Electrolyte leakage from peel or skin that has sunburn browning damage does not appear to differ from the peel or skin of non-sunburned fruit. Thus, sunburned browning of the fruit appears to have little effect on membrane integrity although acceleration of the degradation of chlorophyll occurs. Of note, sunlight/solar irradiation is required for sunburn browning. Although sunburn browning sometimes appears to disappear as fruit matures, the disorder is not reversible. Instead, anthocyanins and other pigments sometimes mask these symptoms as the fruit color develops with maturity.

The third type of sunburn occurs on "non-acclimated" fruit that have been previously shaded and are suddenly exposed to full sunlight, e.g., after thinning or shifting of a branch as fruit load increases. This type of sunburn can occur at much lower air and fruit surface temperatures, such as in the fall. It does require light although it does not appear to require ultraviolet-B exposure. It has been observed in apples that this type of sunburn can occur when the air temperature is only 64° F., and fruit surface temperature is only 88° F. Initial damage is seen within 24 hours as bleaching or whitening of the sun-exposed skin surface. With continued exposure to sunlight, the bleached area turns brown.

In sunburned conditions, most of the cells under the epidermal layer of the fruit are damaged by low moisture content. The more severe form of this damage causes serious changes in the cuticle, and in the epidermal and sub-epidermal tissues. It is often noticed that in sun damaged fruit, the firmness of the flesh increases. This can be explained by the fact that the sunburned plant cells mainly perish because the cell walls thicken, and the tissues lose water and harden.

Sunburn and/or heat stress also can induce or enhance several skin and/or fruit disorders, such as lenticel marking (dark spots), sunburn scald, cracking/splitting, misshapen fruit, bitter pit (blotchiness), "Fuji stain", and watercore. Watercore is a physiological disorder associated with internal moisture stress. High temperatures cause premature localized conversion of starch to sugar and pronounced sap leakage from cells, or an influx of sap into intercellular spaces. This causes a glassy appearance to appear on the surface of the fruit. Sunburned tissues can also serve as entrance points for fungi and other pathogens.

Numerous climate-ameliorating products have been used to reduce sunburn and/or heat stress on crop plants and their fruit. By the term "climate" is meant the environment above the surface of the soil in intimate contact with the surface of the plant and fruit and certain vegetables. Hereinafter, the term "fruit" will mean fruit and those vegetables, such as corn, tomatoes, and cucumbers that pre-harvest are exposed to the climate. The term "plant" means fruit-bearing plants. By the term "climate-ameliorating product" is meant the use of a device, water, or a chemical composition external to the plant or pre-harvest fruit that reduces the amount of heat and/or radiation impacting the surface of the plant or fruit above the surface of the soil. Among the most effective measures are evaporative cooling with water, and the use of sunburn protective coatings also known as particle film technology (PFT), bagging, reflective fabric, and shade netting.

Shade netting, mesh, or cloth can reduce air temperatures under the material by 4° F.-12° F. and increase the ratio of diffuse to direct sunlight on the fruit. The shade material also decreases transpiration rates resulting in increased mid-day water-use efficiency. This system can reduce sunburn, but it is very expensive because it requires a trellis system to hold up the shading material as well as the capability to apply it prior to harvest. Later, it must be removed for normal seasonal tree/vine growth. Excessive shading also negatively affects photosynthesis that, among other effects, will cause problems with flower bloom initiation early in the season and may affect yields. Growers have expressed concern about the deleterious effects that the shading can have on fruit trees, fruit bearing vines, and the soil. The protective mesh often interferes with the full, normal color development of fruit. Uniform shade can also cause an undesirable alteration in the growth habits of trees or vines and can reduce fruit production.

The use of reflective fabric, such as metalized surface plastics, white plastics, and foil materials on the ground of an orchard or vineyard can result in an increase in fruit size and yield with a concomitant reduction in fruit sunburn damage. Also, the fruit is often of a more consistent quality, i.e., of increased color, firmer, size uniformity, and sweetness. However, as with the shade netting, the labor and material costs are a limiting and often deciding factor with regard to the desirability or even feasibility of using this approach.

Evaporative cooling is one of the most efficient ways to reduce fruit surface temperature. The application of low volumes of water, cools the fruit through evaporative cooling of the surrounding air. When water is applied, it also evaporates from the fruit surface and cools the fruit. In addition, it hydrocools the fruit by carrying heat away in runoff. Such a system requires very high quality water with low salt content to prevent residues from being left on the fruit surface and extremely careful management to produce the desired cooling effect without increasing fireblight, apple scab, or root rotting diseases. This water aspersion option often requires an expensive installation; constant water spraying removes agrochemical products previously applied over the trees; and the increase in environmental humidity favors the development of diseases and weeds, affecting as a whole the phytosanitary status of the orchard. Application rates of 40-70 gallons per minute per acre are usually needed to cool fruit on the hottest days.

Although evaporative cooling, as noted above, is an effective means of reducing fruit temperatures and thus fruit damage, the demand for water in agriculture is in competition with urban, industrial, and recreational water demands. As a result, in addition to the expense associated with obtaining high quality water for such an evaporative cooling system, there are currently serious concerns over limited water availability in agricultural production.

Bagging fruit is normally used to control insect and disease pests but can be used to reduce sun damage on fruit. Each fruit or fruit bunch is usually covered with a double bag early in the season as the fruit begins to enlarge. Approximately 3 weeks prior to harvest, the outer bag is removed, exposing a transparent bag that protects the fruit but allows light penetration and good color development. This inner bag is removed just before harvest. This method is extremely expensive but can potentially increase profits if used on specialty fruits.

With respect to sunburn protective, particle film technology, ideally such a protective coating would have at least the following characteristics: (1) be composed of a chemically inert material, (2) spread and create a uniform film, (3) the film be porous so that it does not interfere with gas exchange from the leaf, (4) transmit photosynthetically active radiation but exclude ultraviolet and infrared damaging radiation to some degree, (5) reduce insect/pathogen behavior on the plant, and (6) be easily removed from the harvested fresh-market fruit. The industry is still searching for this perfect protective coating.

Historically, "whitewash" reflective, particle film technology (PFT), has been used to reduce heat stress. These reflective materials (unlike polymer film antitranspirants that physically block the stomates) have antitranspirant plant properties because they lower the leaf temperatures by increasing reflection of infrared radiation. The lowered leaf temperatures reduce the vapor pressure gradient between the leaf and the air, which is the driving force behind the transpiration; thus reducing the transpiration. It is critical that any product sprayed on a plant not interfere with the exchange of carbon dioxide through the stomates, otherwise primary productivity will be reduced. (Some antitranspirants increase stomatal closure to maintain high plant turgor and rigidity by reducing transpiration, but obstructing stomates can also reduce photosynthesis.)

Various commercial, reflective, particle film technology products are currently available that offer sunburn and/or heat stress protection. One of these products, Raynox®, a registered product of FruitGard LLC and manufactured by Pace International, is based on UV-absorbing plant waxes (carnauba wax). This wax deteriorates with solar radiation as time goes by, and as a result, it is usually necessary to apply the product many times to achieve a desirable result (Good Fruit Grower Mag., "Sunburn-reducing Films Compared" G. Warner, 2007).

Another product, Surround®, is described as a PFT product that is applied over the plant and fruit to screen UV and general solar radiation. This product is made from kaolin (mineral clay) as a suspension of finely divided white clay and it not only reflects incident radiation of the fruit but also radiation that reaches the plant leaves. This obviously decreases the efficiency of the photosynthetic processes of the plant, which affects not only its own growth and the growth of its fruit, but also the general health of the plant. This clay suspension can also limit plant transpiration because of stomatal blockage or occlusion. All of these effects cause increased stress to various biosynthetic pathways in the plant and/or a decrease of fruit quality or amount, i.e., their color and size. Also, fruit growth can cause the clay layer to break, thus losing a part of its protective ability, and requiring many applications during fruit growth and ripening. Kaolin formulations are also reported to suffer from substantial application problems such as excessive foaming and "globbing" in spray tanks. Kaolin powders are easily washed off by rain, further necessitating multiple applications or the use of stickers in order to maintain beneficial effects (NY Fruit Quarterly, Vol. 10, No. 1, Spring 2002).

Sunshield®, sold by Agrohytec, is taught to be applied over trees, vines and fruit to filter UV radiation and is described as a biodegradable polymeric protein micro-layer. The mode of action is similar to that of the carnauba wax products.

A recent product, Kool-Kore®, a trademark of OMRI Ltd, Pasco, Wash., is based on a composition of amorphous silica and surfactants, and is said to have a principle action similar to that of the kaolin-based compositions.

Another product is defined as a proprietary mixture of calcium carbonate and clay. These mixtures are reflecting clays and thus operate using the same mode of action.

Growers have disclosed several problems relating to the use of PFT material in general in that the compositions often plug spray nozzles, and require multiple applications that are very labor intensive. Furthermore, these coatings on the fruit after harvest are often difficult to wash off, off-times requiring additional washing and scrubbing procedures. In some cases, growers have been required to install additional wash tanks, use cleaning detergents, change brush lengths and/or shapes, and increase water pressure in the rinses. Even with these extra steps, it has proven difficult to remove coating material from the skin in the well around the stems. This is not a serious concern with fruit destined for further processing such as apples being sold for apple sauce or canning or wine grapes, however it is a major issue for table grapes and other fruit to be sold in the fresh fruit markets.

In summary, there currently is a lack of adequate means to prevent sunburn and/or heat stress in fruit crops. Efforts to date have been directed toward modifying the climate to which the fruit and the fruit plant are exposed. This approach, in addition to being a major expense to the grower as a result of the need for additional installation of equipment and/or being labor intensive, has proven to be fraught with difficulties and less than satisfactory results. Thus there is a strong need in the agricultural and viticultural industries for an inexpensive and effective means to mitigate fruit environmental damage, especially sunburn and/or heat stress damage, that is long lasting; is relatively amenable to easy application by growers; and does not require additional, expensive steps for protective film removal.

The instant invention provides the above-enumerated advantages and, in addition, enhances plant vigor, especially plant growth, fruit yield, density, color, and quality.

SUMMARY OF THE INVENTION

The instant invention provides a process for inducing plants to systemically mitigate the deleterious effects of sunlight and/or heat stress on its fruit by applying the compositions of this invention to the root zone of the plants. The process consists of applying to the plant root zone a bioefficaciously effective amount of a composition comprising an active selected from the group consisting of ethylene oxide-propylene oxide block copolymer, $C_1$-$C_4$ alkyl ether of ethylene oxide-propylene oxide block copolymer, alkyl polyglycoside, and combinations thereof. The application of these compositions to the soil surrounding the root zone of the plant, is unexpectedly able to systemically, significantly ameliorate damage to the fruit thereof resulting from sunlight radiation and/or heat stress exposure.

DETAILED DESCRIPTION OF THE INVENTION

The instant invention relates to the discovery that the deleterious effects of sunlight and/or heat stress on fruit can be significantly and efficiently reduced by applying to the root zone of the plant, a bioefficaciously effective amount of a composition comprising an active selected from the group consisting of ethylene oxide-propylene oxide block copolymer, $C_1$-$C_4$ alkyl ether of ethylene oxide-propylene oxide block copolymer, alkyl polyglycoside, and combinations thereof. This process induces and enables the plant to systemically better tolerate heat stress and protect its fruit.

Additionally, it has been found that compositions containing these compounds are highly efficacious over a wide range of concentrations which is of critical importance in achieving maximum agronomic and/or hydrological benefit while minimizing any possible negative environmental impact.

The ethylene oxide-propylene oxide (EO/PO) block copolymers of the instant invention include the straight block polymeric glycols obtained, for example, by the addition of ethylene oxide (EO) on a condensation product of propylene oxide (PO) with propylene glycol. The block polyoxypropylene cores, being the hydrophobe, have PO units at least about 9, and are usually in the range of from about 950 to about 4,000 mass average molecular weight. The ethylene oxide (EO) is added to the core at from about 10 weight percent to about 80 weight percent. In a preferred embodiment, the polyoxypropylene core mass average molecular weight is from about 1500 to about 2000 with EO addition of from about 20 to about 40 weight percent. Reverse block copolymers, which are also acceptable for use in the instant invention, are prepared by adding ethylene oxide to ethylene glycol to provide a hydrophile of designated molecular weight. Polypropylene oxide is then added to obtain hydrophobic blocks on the outside of the molecule. Reversing the hydrophobic and hydrophilic blocks creates surfactants similar to the regular EO/PO/EO block copolymers, but with some important differences. While the EO/PO/EO straight block copolymers tend to be better emulsifiers and dispersants and cover a broader range of molecular weights, the reverse block copolymers have lower foaming, greater defoaming, and reduced gelling tendencies. Additionally, reverse block copolymers are terminated by secondary hydroxyl groups, which have lower reactivity and acidity than the primary hydroxyl groups that terminate the EO/PO/EO straight block copolymers.

Tetra-functional block copolymers and their reverse counterparts, which are derived from the sequential addition of propylene oxide and ethylene oxide to ethylene diamine are also useful in the compositions of this invention.

Commercially available block polymeric surfactants of this type include those of the Antarox series, e.g., L-62 and L-64 marketed by Rhodia Inc.

The $C_1$-$C_4$ alkyl ethers of ethylene oxide-propylene oxide (EO/PO) block copolymers of this invention can be readily prepared by etherification procedures well known in the art, as for example taught in U.S. Pat. No. 4,922,029. As a specific example, conversion of an ethylene oxide-propylene oxide block copolymer having hydroxyl termination to a methyl ether of the copolymer is readily effected by reacting it with sodium hydroxide and methyl chloride, although it is possible to use metallic sodium in place of the sodium hydroxide, and/or other methyl halides or dimethyl sulfate in place of methyl chloride. In any event, the methyl ether formation is accompanied by the formation of a by-product salt that is separated from the product. The salt can be separated by conventional means such as filtration, decantation, extraction, and/or distillation. In some cases, it is advantageous to conduct the methylation in two or more steps with salt separation after each step.

The $C_1$-$C_4$ alkyl ethers of ethylene oxide-propylene oxide block copolymers of the instant invention include, before etherification, the straight polymeric glycols obtained, for example, by the addition of ethylene oxide on propylene oxide that can be structurally depicted as $HO(CH_2CH_2O)_x(CH(CH_3)CH_2O)_y(CH_2CH_2O)_zH$. The identical or different integers x, y, and z individually are greater than or equal to zero such that the desired propylene oxide and ethylene oxide mass average_molecular weights and percentages are obtained. The polypropylene oxide cores, being hydrophobic, have units at least about 9, and are usually in the range of from about 950 to about 4,000 mass average molecular weight. The ethylene oxide is added to the core at from about 10 weight percent to about 80 weight percent. In a preferred embodiment, the polypropylene oxide core mass average molecular weight is from about 1500 to about 2000 with ethylene oxide addition of from about 20 to about 40 weight percent.

The preferred alkyl ethers of ethylene oxide-propylene oxide block copolymers for use in this invention are those having an HLB value less than or equal to 10; an average molecular weight of from 2,000 to 8,000 and a weight percent hydrophile of less than 40. The most preferred block copolymers are those having an HLB value less than or equal to 10; an average molecular weight of from 2,000 to 8,000 and a weight percent hydrophile of less than 20.

Alkyl polyglycosides are understood to be the reaction products of sugars and fatty alcohols, suitable sugar components being the aldoses and ketoses such as glucose, fructose, mannose, galactose, talose, gulose, allose, altrose, idose, arabinose, xylose, lyxose, lactose, sucrose, maltose, maltotriose, cellobiose, mellobiase, and ribose, which are referred to hereinafter as glycoses. Particularly preferred alkyl polyglycosides are alkyl glucosides by virtue of the ready availability of glucose. In its broadest sense, the term "alkyl" in alkyl polyglycoside is intended to encompass the residue of an aliphatic alcohol, preferably a fatty alcohol, obtainable from natural fats, i.e., saturated and unsaturated residues and also mixtures thereof, including those having different chain lengths. The terms alkyl oligoglycoside, alkyl polyglycoside, alkyl oligosaccharide and alkyl polysaccharide apply to alkylated glycoses of the type in which one alkyl radical in the form of the acetal is attached to more than one glycose residue, i.e., to a polysaccharide or oligosaccharide residue; these terms are generally regarded as synonymous with one another. Accordingly, alkyl monoglycoside is the acetal of a monosaccharide. Since the reaction products of the sugars and the fatty alcohols are generally mixtures, the term alkyl polyglycoside is intended to encompass both alkyl monoglycosides and also alkyl poly(oligo) glycosides.

Optionally, there can be a polyoxyalkylene chain joining the alcohol moiety and the saccharide moiety. The preferred alkoxide is ethylene oxide.

The higher alkyl polyglycosides express surfactant properties. By "higher alkyl polyglycoside" is meant a glycoside having an alkyl substituent that averages more than four carbon atoms in size.

The lipophilic groups in the alkyl polyglycosides are derived from alcohols, preferably monohydric for compatibilizer applications and should contain from 4 to 22, preferably 7 to 16 carbon atoms. While the preferred groups are saturated aliphatic or alkyl, there may be present some unsaturated aliphatic hydrocarbon groups. Thus, the preferred groups are derived from the fatty alcohols derived from the naturally-occurring fats and oils, such as octyl, decyl, dodecyl, tetradecyl, hexadecyl, octadecyl, oleyl and linoleyl, but groups may be derived from synthetically produced Ziegler alcohols or oxo alcohols containing 9, 10, 11, 12, 13, 14 or 15 carbon atoms. The alcohols of naturally-occurring fatty acids, typically containing an even number of carbon atoms and mixtures of alcohols, are commercially available such as mixtures of $C_8$ and $C_{10}$, $C_{12}$ and $C_{14}$, and the like. Synthetically-produced alcohols, for example those produced by an oxo process, contain both an odd and even number of carbon atoms such as the $C_8$, $C_{10}$, $C_{11}$ mixtures.

From their production, the alkyl polyglycosides may contain small quantities, for example 1 to 2%, of un-reacted long-chain alcohol which does not adversely affect the properties of the surfactant systems produced with them.

Specifically, the preferred alkyl polyglycosides for use in the present invention are obtained by the reaction of alkanols with glucose or other mono- or di- or polysaccharides. Preferred alkyl polyglycosides for use in the present invention are the alkyl polyglucosides obtained by the reaction of glucose with a straight or branched chain alkanol or mixture of alkanols, for example, a mixture of alkanols containing 4 to 22, preferably 7 to 16 carbon atoms, for example, 8 to 10 carbon atoms. The number of glucose groups per alkyl group in the molecule may vary and alkyl mono- or di- or polyglucose or saccharide derivatives are possible. Commercial alkylpolyglucosides usually contain a mixture of derivatives having an average number of glycose groups per alkyl group (the Degree of Polymerization or D.P.) of between 1 and 4 for example, preferably from 1 to 2. A number of suitable alkylpolyglycosides are commercially available and include, for example, AL2042 (ICI); AGRIMUL 2069 or AGRIMUL PG 2067 (Cognis) and ATPLUS 438 or ATPLUS 452 (Uniqema).

Illustrative of the many processes available for the preparation of alkyl polyglycosides useful in the present invention are those disclosed in the following U.S. Pat. Nos. 4,950,743; 5,266,690; 5,304,639; 5,374,716; 5,449,763; and 5,457,190.

The ecotoxicity profiles of the alkyl polyglycosides show them to be among the most environmentally friendly of the nonionic surfactants and with the exception of Cognis's Agrimul PG 2067, are reported to be strong wetting agents (Alkyl Polyglycosides: Technology Properties and Applications edited by Hill, et al. —New Solutions for Agricultrual Applications; R. Garst; Chapter 7; pages 131-137).

Concentrations of the polymer compositions of this invention in the aqueous formulations to be applied to the plant root zone in the soil are not critical. Composition levels of up to 200,000 ppm are contemplated in this invention for those concentrations are non-injurious to most plants. Thus, the concentration of the polymeric active ingredients of this invention in the aqueous formulations will range from about 200,000 to about 2 ppm; preferably from about 120,000 to about 5 ppm.

The most bioefficacious application rates of the polymer actives to the root zone soil have been found to be in the range of from about 0.0001 to about 25 Kg per hectare; preferably from about 0.001 to about 15 Kg per hectare; and most preferably from about 0.005 to about 10 Kg per hectare. These application rates reflect individual applications or the cumulative amounts resulting from multiple applications within a limited but bioefficacious period of time.

One of the surprising features of the use of these compositions is the outstanding effectiveness at very low concentrations: a highly desirable environmental property. In any event, appropriate concentration levels are easily determined by those skilled in the art.

Although the processes of this invention are especially bioefficacious on crops such as apples and grapes, the invention is also very useful in all crops where heat stress and/or sunburn may impact plant productivity and fruit quality. Examples include citrus fruits (including oranges, lemons, limes, grapefruit), solanaceous plants (including tomatoes and peppers), cucurbits (including cucumbers, squash, pumpkin, rock melon, honeydew melon, watermelon, and cantaloupe). Other plants include stone fruits (such as peaches, cherries, nectarines, almonds, and plums), strawberries, raspberries, blueberries, and olives; and tropical crop such as avocados, bananas, mangos, and pineapple. In this invention, the term fruit is meant broadly to include other produce exposed to the radiation of the sun.

Results realized by using the instant invention are exemplified below; however definitions and the test procedures utilized will first be clarified.

By the term "bioefficaciously effective amount" is meant the amount of the polymeric active ingredients of this invention in contact with the soil such that there is a measurable decrease in heat stress and enhancement of sunburn protection in fruit, e.g., a measurable reduction in observable environmental damage to the fruit from plants in the treated soil.

Other than in the operating examples, or where otherwise indicated, all numbers expressing quantities of ingredients or reaction conditions used herein are to be understood as modified in all instances by the term "about".

The invention will now be described with reference to a number of specific examples that are to be regarded solely as illustrative of the methods and compositions of this invention and not as restrictive of the scope thereof. All percentages are by weight unless otherwise indicated.

EXAMPLES

The following three examples illustrate the significant decreases in heat stress and sunburn of horticultural crops that can be realized by utilizing the processes of this invention. Specifically, Example I depicts the application of the compositions of this invention to soil and the resulting unanticipated effects on plant heat stress protection in an apple orchard and Examples II and III, the use of said compositions in vineyards.

The horticultural sites in all of the examples were treated in essentially the same manner. AAGG, a proprietary composition of Aquatrols Corporation of America, Inc. comprising a 0.7:1 weight ratio of an alkyl glycoside and an hydroxy terminated ethylene oxide-propylene oxide block copolymer was prepared at a concentration of 170 grams/liter (g/l) of the active ingredients (AAGG). Initially, a rate of 10 liters/hectare (liters/ha) and 5 liters/hectare (liters/ha) of this formulation was applied by a hand held small plot spray boom in the apple orchard which was irrigated by mini-sprinklers. Since the vineyards had drip irrigation, 100 mls of AAGG (17% ai) was mixed in 900 mls of water and initially a rate of 10 mls and 5 mls of this solution was applied under each dripper with the assumption that one dripper covered an area of one square meter, this was essentially equivalent to 10 and 5 liters/ha. Approximately monthly, follow-up applications were made in the same manner with 5 and 2.5 mls of this solution respectively, i.e., essentially 5 and 2.5 liters/ha. Water irrigation followed one to three days following each application.

The trials were conducted as replicated studies in a randomized complete block design. In Examples I through II, the trials were replicated six times; in Example III, five times. In the orchard trial, in Example I, the plot size was 12.5 m in length by 2 m in width and each plot contained 5 apple trees. In the vineyard Example II, the plot size was two panels of vines comprising 8 vines in length by 1 m in width. In Example III, the plot size was two panels each consisting of 4 vines. Data was recorded and statistically analyzed using an analysis of variance with mean values summarized and separated using Least Significant Test at the 5% level of probability.

Example 1

In this first example, the procedures of this invention were applied to an orchard comprised of 6 year-old Gala apple trees. Over the three-month duration of the applications, the temperatures were well above average with 35 days having temperatures above 30° C. and 10 days wherein the temperatures exceeded 35+ C. Two rainfalls provided respite periods of soil moisture in an otherwise very dry tree-line environment. Overall, the trial period was hot and dry. Even with the rainfalls, the tree blocks were in deficit irrigation during the application period. The blocks were estimated to be at an approximately 75% water deficit.

During the first month, all trees were thinned to 105 apples per tree. The crop in this orchard was relatively light due to frost damage and a failure to adequately water and fertilize during the previous season. At harvest, all of the apples from the two center trees were harvested.

At harvest, the heat stress effects were identified as either good quality or severely sunburned apples. All of the apples that showed severe sunburn symptoms were counted on each tree. Table I shows the results of the sunburn damage to the fruit from the treated trees as compared to the untreated controls.

TABLE I

Sunburned Apples Results

| Treatment | Rate (liters/ha) | Sunburned Apples/Tree | Percent Apples Sunburned |
|---|---|---|---|
| Untreated Control |  | 10.8 a | 11.3 a |
| AAGG | 5/2.5 | 5.2 b | 5.5 b |
| AAGG | 10/5 | 3.2 b | 3.3 c |
| Untreated Control |  | 9.5 a | 9.9 a |
| LSD (P = 0.05) |  | 2.09 | 2.12 |
| Standard Deviation |  | 1.7 | 1.72 |
| CV |  | 23.67 | 23.01 |

Means in columns followed by the same letter, do not significantly differ (P = 0.05, LSD)

The data clearly shows that the addition of the AAGG to the apple tree-root zones has significantly reduced the level of sunburn damage in the fruit compared to that from the untreated trees. The percent of the severely damaged fruit has been reduced from 11.3 and 9.9% (mean of 10.6%) in the untreated trees to 5.5% in the 5/2.5 liters/ha application rate trees and even down to 3.3% from the trees subject to the higher 10/5 liters/ha AAGG application rates.

Thus the application of the AAGG of this invention to the apple orchard soil unexpectedly has systemically protected the fruit from sun and/or heat stress damage.

Example II

In this second example, the procedures of this invention were applied to a vineyard comprised of "Shiraz" wine grape vines. Over the four-month duration of the applications—the grapes were harvested at the end of the fifth month—the temperatures were well above the long term averages for those specific months and the number of days wherein the temperatures exceeded 30° C. was also greater than the long term average. In the month before harvesting, the average temperature was slightly cooler than normal for that month, i.e., about 1.5° C. below the long-term average.

Two rainfalls, one in the middle of the second month and one in the middle of the third month, provided some soil moisture in an otherwise very dry vineyard environment. Overall, the trial period was relatively hot with fruit growers operating on minimal water allocations. Even with the rainfalls, the grape vines were in deficit irrigation during the application period. The plots were estimated to be at an approximately 70% water deficit.

At harvest, all of the bunches of grapes from the 8 vines in each plot were rated for the incidence of sunburn and/or heat stress damage. Each bunch was individually rated according to the rating system detailed in Table II and the results set forth in Table III below.

TABLE II

Sunburn/Heat Stress Rating System

| Rating | Incidence of Sunburn/Heat Stress on Grape Bunches (%) |
| --- | --- |
| 1 | 0 |
| 2 | 1-5 |
| 3 | 6-10 |
| 4 | 11-25 |
| 5 | 26-50 |
| 6 | 51-100 |

TABLE III

Treatment Effect on Heat Stress Damage

| | | Percent of Bunches in Each Category Rating | | | | |
| --- | --- | --- | --- | --- | --- | --- |
| Treatment | Rate (liters/ha) | % Rating 1 | % Rating 2 | % Rating 3 | % Rating 4 | % Rating 5 |
| Untreated Control | | 32.7 b | 49.6 a | 14.4 a | 2.6 a | 0.7 a |
| AAGG | 5/2.5 | 62.5 a | 35.6 b | 1.6 b | 0.2 b | 0 a |
| AAGG | 10/5 | 61.9 a | 36 b | 2.1 b | 0 b | 0 a |
| Untreated Control | | 32.7 b | 48.2 a | 16.4 a | 2.7 a | 0 a |
| LSD (P = 0.05) | | 3.71 | 4.52 | 2.37 | 1.3 | 0.7 |
| Standard Deviation | | 3.01 | 3.67 | 1.93 | 1.06 | 0.57 |
| CV | | 6.35 | 8.67 | 22.31 | 76.04 | 335.54 |

Means in columns followed by same letter do not significantly differ
(P = 0.05, LSD)

The application of AAGG compositions at both the 5/2.5 and 10/5 concentrations to the vineyard soil has clearly increased the number of bunches of grapes with no heat stress damage (Rating 1) when compared to the untreated control. The 62% (approx.) of Rating 1 bunches of the treated vines compared to the Rating 1 bunches of the untreated control at 32.7% (approx.) represents almost a doubling in the number of bunches obtained with no heat stress and/or sun damage.

Thus the application of the AAGG of this invention to vineyard soil unexpectedly has systemically protected the grapes from sun and/or heat stress damage.

Example III

In this third example, the procedures of this invention were again applied to a vineyard comprised of "Shiraz" wine grape vines.

Over the four-month duration of the applications—the grapes were harvested at the end of the fifth month—the temperatures and rainfall were identical to that set forth in Example II above, i.e., the temperatures were well above the long-term averages for those specific months and two rainfalls provided some soil moisture in an otherwise very dry vineyard environment. Overall, the trial period was relatively hot with fruit growers operating on minimal water allocations. Even with the rainfalls, the grape vines were in deficit irrigation during the application period. The plots were estimated to be at an approximately 70% water deficit.

At harvest, all of the bunches of grapes from the 8 vines in each plot were rated for the incidence of sunburn and/or heat stress damage. Each bunch was individually rated according to the rating system detailed in Example II above.

TABLE IV

Treatment Effect on Heat Stress Damage in Example III

| Treatment | Rate (liters/ha) | % Rating 1 | % Rating 2 | % Rating 3 | % Rating 4 | % Rating 5 |
|---|---|---|---|---|---|---|
| Untreated Control | | 40.8 a | 36.4 a | 17.8 a | 3.9 a | 1.1 a |
| AAGG | 5/2.5 | 60.8 b | 28.7 ab | 10.2 b | 0.3 a | 0 a |
| LSD (P = 0.05) | | 8.4 | 8.93 | 6.4 | 3.84 | 1.2 |
| Standard Deviation | | 6.09 | 6.48 | 4.64 | 2.78 | 0.87 |
| CV | | 9.68 | 24.17 | 52.33 | 248.74 | 319.98 |

Means in columns followed by same letter do not significantly differ
(P = 0.05, LSD)

The application of AAGG compositions has significantly reduced the incidence of heat stress and sunburn on the grapes. This is clearly shown by the significant increase in the percentage of bunches of grapes with no damage (Rating 1) when compared to bunches of grapes on the untreated control. The untreated vines only had 40.8% of the bunches with no damage, while the application of the AAGG composition resulted in 60.8% with no damage; about a 50% reduction in damaged grapes.

Thus the application of the AAGG of this invention to vineyard soil has unexpectedly, systemically protected the grapes from sun and/or heat stress damage. The inherent advantage of the AAGG treatment is that statistically significant, commercially relevant reductions in heat stress damage (sunburn) can be achieved by applying a composition to the soil which systemically induces heat stress protection and does not necessitate utilization of additional processes to protect the plant and/or fruit from heat stress and/or sunburn damage. However, also within the scope of this invention is the use of the systemically induced protection of this invention in conjunction with the use of a climate-ameliorating product; the preferred being a particle film technology product, to enhance the beneficial results.

It is anticipated that the compositions of this invention can also be blended with soil active or soil directed pesticides or fertilizers.

It is also anticipated that the liquid compositions of the instant invention be also utilized in solid form, such as powder or granular form, e.g., by either being added to and/or blended with inert filler material, biological actives, such as pesticides and fertilizers, and/or other additives, such as adjuvants in methods well known by those skilled in the agrochemical water dispersible or dry spreadable art. In this way, the compositions are able to be delivered in solid form to the root system of the plant growth site and additional control of the release of the compositions can be achieved if one so desires.

Although this invention has been described in detail with particular reference to preferred embodiments thereof, it will be understood that variations and modifications can be effected within the spirit and scope of this invention as described hereinabove and as defined in the appended claims.

Having thus described the invention, what I claim is:

1. A method for systemically mitigating environmental stress from heat or radiation on a fruit plant and the pre-harvested fruit thereof that comprises the steps of:
    preparing an agricultural composition wherein said composition comprises an ethylene oxide-propylene oxide block copolymer, a $C_1$-$C_4$ alkyl ether of ethylene oxide-propylene oxide block copolymer, and an alkyl polyglycoside; and
    intimately contacting root zone soil of soil containing a fruit plant with a bioefficaciously effective amount of said agricultural composition to systemically mitigate environmental stress on the plant and the pre-harvested fruit thereof from heat or radiation impacting the surface of the plant or fruit above the surface of the soil, and wherein the bioefficaciously effective amount is from about 1 g to about 15,000 g per hectare.

2. The method of claim 1 comprising the additional step of:
applying a climate-ameliorating product to the plant and/or pre-harvested fruit.

3. The method of claim 2 wherein the climate-ameliorating product is a particle film technology product.

4. The method of claim 1 wherein the plant is an apple tree.

5. The method of claim 1 wherein the plant is a grape vine.

6. A method for systemically mitigating environmental stress from heat or radiation on a fruit plant and the pre-harvested fruit thereof that comprises the steps of:
preparing an agricultural composition wherein said composition comprises an alkyl polyglycoside and a $C_1$-$C_4$ alkyl ether of ethylene oxide-propylene oxide block copolymer; and
intimately contacting root zone soil of soil containing a fruit plant with a bioefficaciously effective amount of said agricultural composition to systemically mitigate environmental stress on the plant and the pre-harvested fruit thereof from heat or radiation impacting the surface of the plant or fruit above the surface of the soil, and
wherein the bioefficaciously effective amount is from about 1 g to about 15,000 g per hectare.

7. The method of claim 6 comprising the additional step of: applying a climate-ameliorating product to the plant and/or pre-harvested fruit.

8. The method of claim 7 wherein the climate-ameliorating product is a particle film technology product.

9. The method of claim 6 wherein the plant is an apple tree.

10. The method of claim 6 wherein the plant is a grape vine.

11. A method for systemically mitigating environmental stress from heat or radiation on a fruit plant and the pre-harvested fruit thereof that comprises the steps of:
preparing an agricultural composition consisting of water, ethylene oxide-propylene oxide block copolymer, and alkyl polyglycoside; and
intimately contacting root zone soil of soil containing a fruit plant with a bioefficaciously effective amount of said agricultural composition to systemically mitigate environmental stress on the plant and the pre-harvested fruit thereof from heat or radiation impacting the surface of the plant or fruit above the surface of the soil, and
wherein the bioefficaciously effective amount is from about 1 g to about 15,000 g per hectare.

12. The method of claim 11 comprising the additional step of: applying a climate-ameliorating product to the plant and/or pre-harvested fruit.

13. The method of claim 12 wherein the climate-ameliorating product is a particle film technology product.

14. The method of claim 11 wherein the plant is an apple tree.

15. The method of claim 11 wherein the plant is a grape vine.

16. A method for systemically mitigating environmental stress from heat or radiation on a fruit plant and the pre-harvested fruit thereof that comprises the steps of:
preparing an agricultural composition wherein said composition comprises a $C_1$-$C_4$ alkyl ether of ethylene oxide-propylene oxide block copolymer; and
intimately contacting root zone soil of soil containing a fruit plant with a bioefficaciously effective amount of said agricultural composition to systemically mitigate environmental stress on the plant and the pre-harvested fruit thereof from heat or radiation impacting the surface of the plant or fruit above the surface of the soil, and
wherein the bioefficaciously effective amount is from about 1 g to about 15,000 g per hectare.

17. The method of claim 16 comprising the additional step of: applying a climate-ameliorating product to the plant and/or pre-harvested fruit.

18. The method of claim 17 wherein the climate-ameliorating product is a particle film technology product.

19. The method of claim 16 wherein the plant is an apple tree.

20. The method of claim 16 wherein the plant is a grape vine.

* * * * *